(12) United States Patent
Kolb et al.

(10) Patent No.: US 10,830,758 B2
(45) Date of Patent: Nov. 10, 2020

(54) SYSTEMS AND METHODS ENABLING PATCH-CLAMP RE-USE

(71) Applicant: Georgia Tech Research Corporation, Atlanta, GA (US)

(72) Inventors: Ilya Kolb, Atlanta, GA (US); William Stoy, Atlanta, GA (US); Erin Rousseau, Clifton Park, NY (US); Craig R. Forest, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 549 days.

(21) Appl. No.: 15/232,770

(22) Filed: Aug. 9, 2016

(65) Prior Publication Data

US 2017/0038364 A1    Feb. 9, 2017

Related U.S. Application Data

(60) Provisional application No. 62/202,858, filed on Aug. 9, 2015.

(51) Int. Cl.
  *G01N 33/487* (2006.01)
  *B01L 3/02* (2006.01)

(52) U.S. Cl.
  CPC ........ *G01N 33/48728* (2013.01); *B01L 3/022* (2013.01); *B01L 13/00* (2019.08); *B01L 2300/0896* (2013.01)

(58) Field of Classification Search
  CPC .............................................. G01N 33/48728
  See application file for complete search history.

(56) References Cited

U.S. PATENT DOCUMENTS

| 6,776,896 B1* | 8/2004 | Osipchuk ......... G01N 33/48728 204/403.01 |
| 2003/0022268 A1 | 1/2003 | Lepple-Wienhues |
| 2004/0058423 A1* | 3/2004 | Albritton ......... G01N 27/44743 435/173.7 |
| 2004/0146849 A1* | 7/2004 | Huang ............. G01N 33/48728 435/4 |
| 2006/0251544 A1* | 11/2006 | Taboryski ........... B01L 3/50273 422/400 |
| 2011/0251102 A1* | 10/2011 | Osipchuk ............. B01L 3/5085 506/10 |

(Continued)

FOREIGN PATENT DOCUMENTS

JP    WO2013145289    * 10/2013 ............... C11D 7/36

OTHER PUBLICATIONS

Search Report and Written Opinion from related PCT Application No. PCT/US16/49460 dated Dec. 8, 2016 (10 pages).

(Continued)

*Primary Examiner* — Gurpreet Kaur
(74) *Attorney, Agent, or Firm* — Troutman Pepper Hamilton Sanders LLP; Ryan A. Schneider

(57) ABSTRACT

A method for cleaning patch-clamp glass pipette electrodes that enables their re-use. By immersing pipette tips or planar patch clamp chips into a detergent, followed by rinsing, pipettes and planar patch clamp chips were re-usable at least ten times with little to no degradation in signal fidelity, in experimental preparations ranging from human embryonic kidney cells to neurons in culture, slices, and in vivo.

26 Claims, 12 Drawing Sheets

(56) References Cited

U.S. PATENT DOCUMENTS

2012/0252877 A1\* 10/2012 Lo .......................... A61P 25/00
                                                                                      514/44 R
2014/0228857 A1\* 8/2014 Kodandaramaiah ........................
                                                                               A61B 5/6885
                                                                                  606/130
2016/0045918 A1\* 2/2016 Lapham .................. B01L 3/021
                                                                                  506/23

OTHER PUBLICATIONS

Kao, et al., "A New Technique for Multiple Re-use of Planar Patch Clamp Chips" J Neurosci Methods, Jul. 15, 2012.

Malboubi, et al., "Gigaseal Formation in Patch Clamping," Chapter 2, "Development of Patch Clamping" SpringerBriefs in Applied Sciences and Technology (2014).

Bruggemann, et al., "Microchip Technology for Automated and Parallel Patch-Clamp Recording," Small. vol. 2(7) (2006) pp. 840-846.

EP Search Report for application No. EP 16836035 dated Mar. 11, 2019.

Kolb, et al., "Cleaning Patch Clamp Pipettes Enables Their Reuse," Biophysical Journal vol. 110, No. 3., p. 149A Feb. 16, 2016.

Milligan, et al., "Robotic Multiwell Planar Patch-Clamp for Native and Primary Mammalian Cells," Nature Protocols, vol. 4, No. 2, pp. 144-255 Feb. 5, 2009.

\* cited by examiner

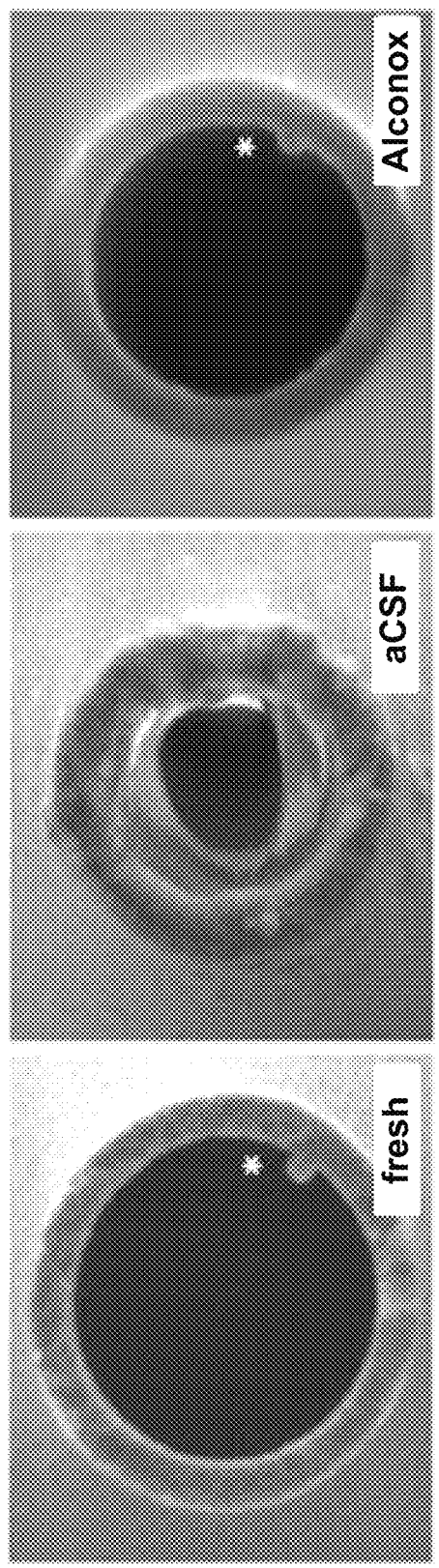

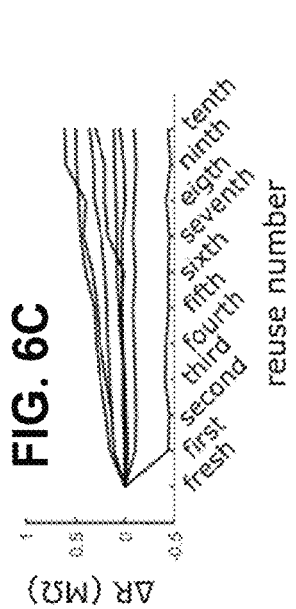
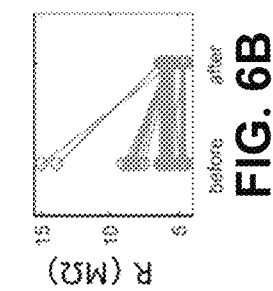
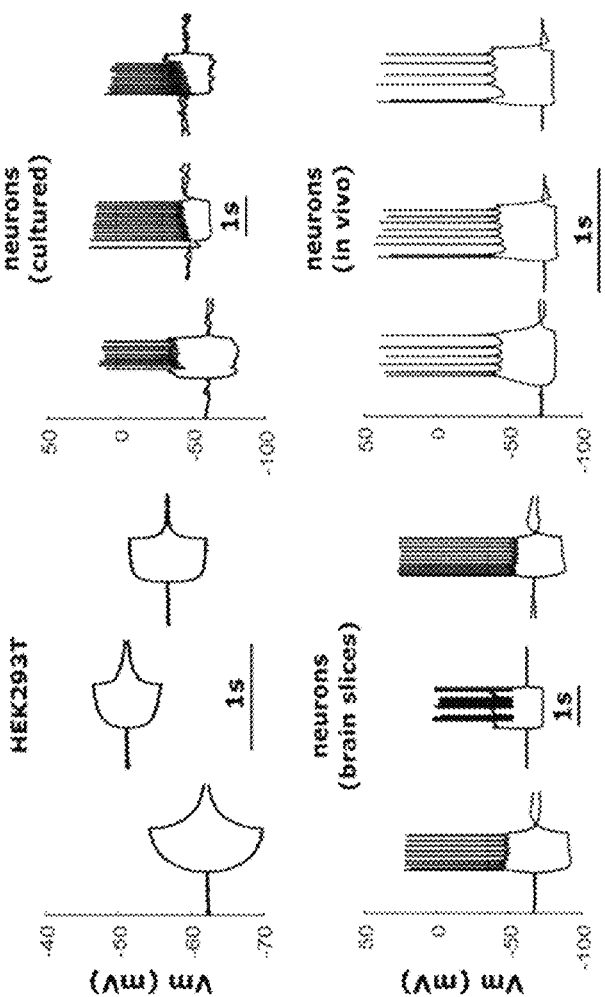
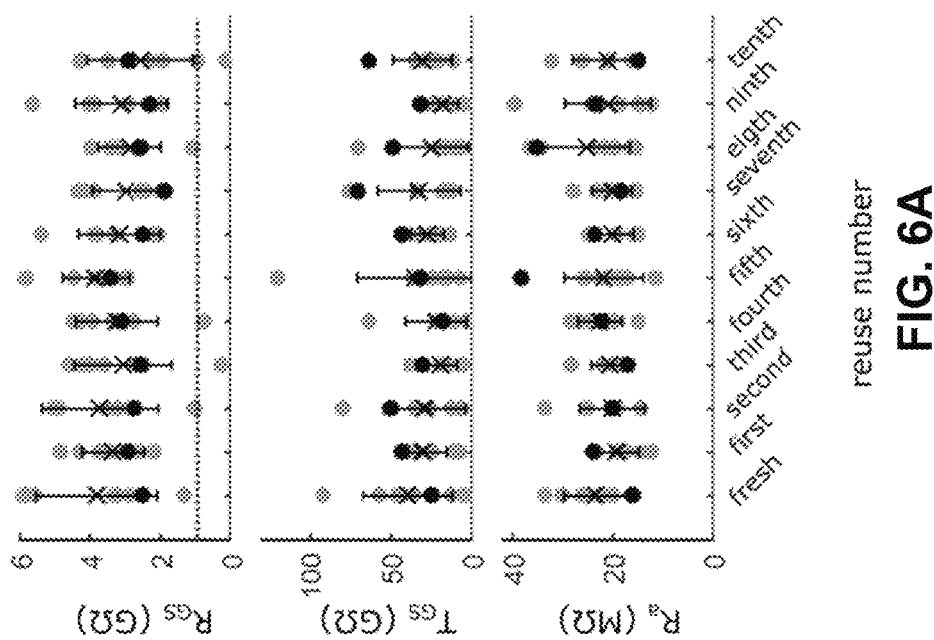

*Sodium (C10-C12) Alkylbenzene Sulfonate (LAS)*

FIG. 11A
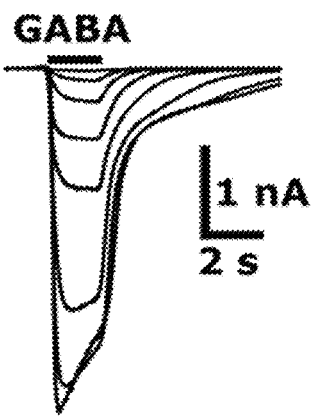
FIG. 11B
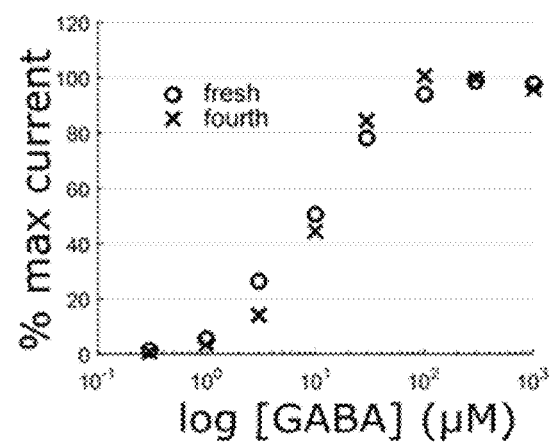
FIG. 11C        FIG. 11D
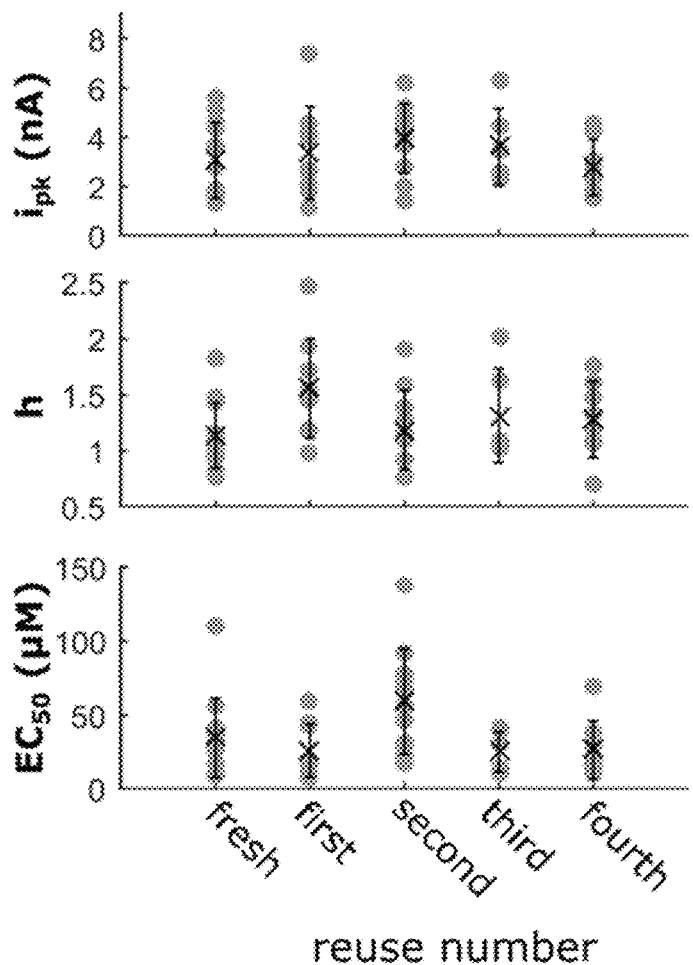
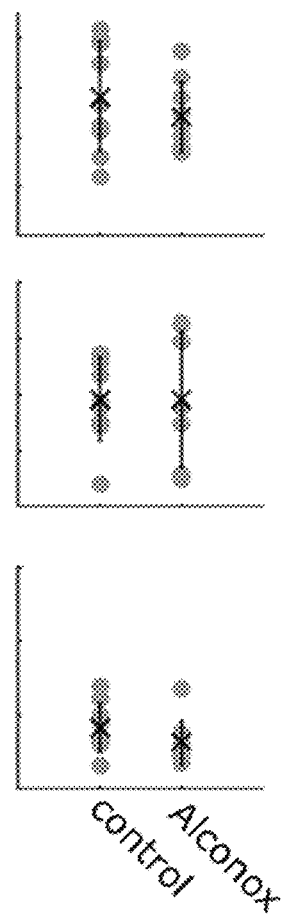

SYSTEMS AND METHODS ENABLING PATCH-CLAMP RE-USE

CROSS-REFERENCE TO RELATED APPLICATIONS

This application claims the benefit of U.S. Provisional Application No. 62/202,858 filed 9 Aug. 2015 the entire contents and substance of which is hereby incorporated by reference.

STATEMENT REGARDING FEDERALLY SPONSORED RESEARCH OR DEVELOPMENT

This invention was made with Government support under Contract No. MH106027, awarded by the National Institutes of Health. The Government has certain rights in the invention.

BACKGROUND OF THE INVENTION

1. Field of the Invention

The present invention relates to pipette cleaning systems and methods, and more particularly to systems and methods of cleaning patch-clamp electrodes.

2. Description of Related Art

Patch-clamp recording is a gold-standard single-cell electrophysiology technique that has been widely used to discover foundational biophysical properties of excitable cells. In neuroscience, the superior sensitivity and resolution of patch-clamp recording has made it an indispensable tool for discovering the tenants of ion channel activity, synaptic integration, plasticity and network connectivity in a variety of experimental preparations from cultured cells to living tissue.

Many pathological conditions such as migraine, hypertension and hypersomnia arise from dysfunctions in cell membrane-bound ion channels. Patch clamp recording is the highest resolution tool available to measure the responses of these channels to drug treatments. Patch-clamp recording provides an unprecedented ability to measure extremely small (on the order of $10^{-12}$ Amperes) electrical currents arising as a result of single or multiple ion channels trafficking charged ions across the cell membrane.

There is a growing demand for large-scale single-cell measurements of electrical and molecular activity; for example for drug screening, cell type characterization, and biophysical analysis. Patch-clamp is well-suited for such studies because it can sample electrical, morphological and genetic properties of single cells and even sub-cellular compartments; however, the technique is not readily scalable.

Patch-clamp recording involves pressing a glass micropipette (namely the aperture) against a cell membrane to achieve a high-resistance (>1 G$\Omega$) seal, or "gigaseal", with the cell membrane. These gigaseals only form when using clean micropipettes, necessitating an operator to replace the contaminated pipette with a fresh one between every contact with a cell membrane. This is a major barrier to facilitating high-throughput drug screening.

In this "conventional" approach to patch-clamp recording, a glass patch-clamp electrode (a hollow glass capillary pulled to a fine ~1 μm diameter aperture at the distal end) is gently pressed against the membrane of a cell, typically under microscope guidance. A brief application of suction to the pipette forces the cell membrane to fully occlude the aperture at the distal end of the electrode. This results in the formation of an intimate physical connection between the cell membrane and the pipette aperture, termed a "gigaseal" because the resistance between the membrane-occluded pipette aperture and an extracellular ground electrode is equal to or greater than 1 gigaohm.

In both conventional and planar patch-clamp systems, to achieve a successful recording, the patch-clamp aperture must have a clean tip to form a high-resistance ($\geq$1 G$\Omega$) junction with the cell membrane. In his Nobel Prize lecture, Edwin Neher remarked that "a gigaseal could be obtained reproducibly when suction was combined with some simple measures to provide for clean surfaces, such as using a fresh pipette for each approach and using filtered solutions". However, the need for a fresh pipette for each approach or a new planar chip is a major limitation to automation and throughput. In conventional systems, the ubiquitous practice of exchanging pipettes requires dexterity from the experimenter, especially when performing simultaneous patch-clamp recordings with multiple pipettes. In planar patch-clamp systems, the need to replace chips after every recording comes at a significant cost to the user.

Further, some promising studies are impractical at large scales because pipettes are not easily replaceable, for instance if they are coated, custom-manufactured, or filled with precious molecules such as synthetic peptides, novel therapeutics, human patient samples or nucleic acid constructs.

As noted above, and confirmed by Dr. Neher, it is widely accepted that cleanliness of the electrode is paramount for the formation of a gigaseal and that once an electrode has come in contact with a cell membrane, the electrode cannot be used to form a subsequent gigaseal with another cell due to adherent cellular debris. This necessitates using fresh electrodes for every patch-clamp trial in both conventional and planar patch systems.

It is thus an intention of the present invention to provide a simple, fast, and automated method for cleaning glass pipette electrodes that enables their immediate re-use. By enabling a single pipette to carry out multiple patch-clamp recordings, full automation of the technique could be achieved which would increase throughput dramatically.

BRIEF SUMMARY OF THE INVENTION

The present invention presents systems and in-situ methods for effectively removing biological debris from patch-clamp electrodes, including conventional glass pipettes and planar patch chips, to enable them to repeatedly re-used.

In exemplary embodiments, effectively removing biological debris is accomplished via cleaning the area where the biological debris is located. This can be done with a cleaning step, a cleaning step and a rinsing step, and with other methods of effectively removing biological debris from proximity of the aperture that forms the seal so the same sealing assembly can be re-used to make another seal with a different cell.

While the present invention refers to systems and methods enabling patch-clamp re-use, and particularly pipettes and planar patch chips, it will be understood by those of skill in the art that the present invention can apply to other environments where, for example, apertured surfaces that are in proximity to or in contact with with biological material, like cell membranes, can benefit from an inventive way of effectively removing biological debris so the same apertured surface can be used once again.

Thus, in some exemplary embodiment, the present invention refers to systems and methods enabling re-use of an apertured surface that is exposed to biological material(s). In a particular embodiment, the apertured surface is the aperture of a pipette used in patch-clamp systems and methods. The problem of continuingly exchanging a patch-clamp electrode for a fresh one can be circumvented by removing cellular debris from a previously-used electrode aperture, thus enabling the same electrode to be used again. The present invention can utilize an electrode cleaning step that enables the re-use of a single electrode in multiple sequential patch-clamp trials, and commoditizes the use of custom-geometry electrodes. The present invention thus reduces a user's expenses associated with electrodes and intra-electrode electrolytic solution.

In another particular embodiment, the apertured surface is one or more of the many apertures of planar patch chips.

In an exemplary embodiment, the present invention effectively removes biological debris from the apertured surface so it can be re-used to achieve gigaseals. In another exemplary embodiment, it is understood that not every surface needs such extreme cleaning. For example, in some conventional planar patch-clamp systems, to be effective, the seal of resistance can be ≤1 GΩ, for example 20-250 MΩ. The present invention is effective in such systems to enable re-use of the apertured surfaces of this kind of planar patch-clamp systems.

The present invention provides a technique for re-using planar patch-clamp chips where the cleaning step does not require the planar chip to be manually extracted from the patch-clamp device to be chemically treated and dried.

The present invention provides a re-use technique applicable to the delicate electrode tip of a patch-clamp pipette. The aperture of patch-clamp electrodes are generally from 0.5-10 μm, much smaller than that of capillaries used for electrophoresis (20-200 μm), making the presently inventive methods distinct from the art of cleaning capillaries used for electrophoresis.

In an exemplary embodiment, the present invention comprises a method of detecting one or more characteristics of cells comprising forming a resistance seal with a membrane of a cell with an apertured surface, forming a resistance seal with a membrane of a different cell with the apertured surface, and preparing the apertured surface, wherein preparing the apertured surface enables re-use of at least portions of the same apertured surface with the different cells.

In an exemplary embodiment, pipettes and planar patch chips are re-used (apertured surfaces are re-used) via cleaning. Other systems and methods of clearing biological debris from the proximity of the aperture to enable re-use are contemplated. For example, apertured surfaces can be treated with a gas, heated, etched with an ion beam, melted and reformed, sputter coated, or otherwise treated to enable re-use of the same apertured surface with a number of different cells.

Some conventional planar patch-clamp systems only achieve a loose-seal recording that amounts to a seal of resistance ≤1 GΩ, for example 20-250 MΩ. While this does not enable high-resolution whole-cell recording, is still useful for studying ion channels. The present invention remains useful in such planar patch-clamp embodiments to enable re-use of one or more of the apertured surface(s) with different cells, even if the seal of resistance ≤1 GΩ.

In other exemplary embodiments, the resistance of each resistance seal can be ≥1 GΩ.

At least portions of the same apertured surface can form a resistance seal with a membrane of at least five different cells, and wherein the resistance of each resistance seal is ≥1 GΩ.

At least portions of the same apertured surface can form a resistance seal with a membrane of at least seven different cells, and wherein the resistance of each resistance seal is ≥1 GΩ.

Preparing the apertured surface can occur in-between each step of forming a resistance seal with a membrane of a cell.

Preparing the apertured surface can comprise subjecting the apertured surface to a cleaning solution.

Preparing the apertured surface can comprise subjecting the apertured surface to a cleaning solution and a rinse solution.

The apertured surface can comprise the aperture of a pipette.

The apertured surface can comprise the aperture in a planar electrode.

The aperture of the pipette or planar electrode can have a diameter between 0.5-10 μm.

In another exemplary embodiment, the present invention comprises a method of repeatedly electronically isolating currents measured across a membrane of a cell comprising forming a resistance seal with a membrane of a cell with an apertured surface, repeating the step of forming a resistance seal with a membrane of a cell with at least seven different cells with the same apertured surface, and preparing the apertured surface at least once in-between two consecutive steps of forming a resistance seal with a membrane of a cell, wherein preparing the apertured surface enables re-use of the same apertured surface with the different cells, and wherein each resistance seal is ≥1 GΩ.

In another exemplary embodiment, the present invention comprises system for detecting one or more characteristics of cells comprising an apertured surface used for forming a resistance seal with a membrane of a cell, and a re-use assembly, wherein the re-use assembly prepares at least portions of the apertured surface so it can be re-used to form a resistance seal with a membrane of at least two different cells.

The system can further comprise a suction assembly in communication with the apertured surface and providing a resistance for each resistance seal of ≥1 GΩ.

The re-use assembly can comprise a cleaning solution.

The re-use assembly can comprise a rinse solution.

In another exemplary embodiment, the present invention is a method of removing biological debris from a patch-clamp electrode comprising one or more chemical treatments applied sequentially to wash the inner and outer surfaces of at least a portion of the electrode by the agency of pneumatic pressures applied to the electrode lumen.

The patch-clamp electrode can be a micropipette formed of a hollow glass capillary pulled to a fine tip with an aperture diameter between 0.5-10 μm at its distal end.

The patch-clamp electrode can be a planar patch chip.

One of the chemical treatments can comprise a composition comprising sodium bicarbonate, sodium (C10-C16) linear alkylbenzene sulfonate (LAS), sodium tripolyphosphate, tetrasodium pyrophosphate, sodium carbonate, and sodium alcohol sulfate dissolved in deionized water.

A final chemical treatment can be non-cytotoxic. The final chemical treatment can be buffered solution where the pH is within the range 7.2 to 7.5 and the osmolarity is within the range 290-320.

The agency of pneumatic pressures can comprise alternating positive and negative pressures (up to ±1,500 mbar) relative to atmosphere to bring the cleaning solution in contact with the electrode interior surface for a specified time interval.

The application of pneumatic pressures can be controlled by a computer or microcontroller.

The electrode can be moved between chambers containing chemical treatments using a three-axis micromanipulator.

In an exemplary embodiment, a first aCSF (artificial cerebrospinal fluid) wash is performed (−200 mbar-10 seconds, 200 mbar-30 seconds), a cleaning agent is cycled preferably six times (−200 mbar-10 seconds, 200 mbar-30 seconds), and a second aCSF wash is performed (−200 mbar-10 seconds, 200 mbar-30 seconds).

In another exemplary embodiment, the present invention comprises systems and methods for cleaning patch-clamp glass pipette electrodes that enable their re-use. By immersing pipette tips into a detergent, followed by rinsing, pipettes were re-usable at least ten times with little to no degradation in signal fidelity, in experimental preparations ranging from human embryonic kidney cells to neurons in culture, slices, and in vivo.

In another exemplary embodiment, pipette tips are immersed into Alconox (Alconox Inc), a commercially-available detergent, at 2% w/v (20 mg/ml), for 60 seconds, which permits multiple re-uses in cell cultures, tissue slices, and in vivo. There was no detectable Alconox in the pipette after cleaning, and ion channel pharmacology results were indistinguishable between fresh and cleaned pipettes. The present pipette cleaning method for the first time enables dramatically improved automation of patch-clamp, as demonstrate with unattended, sequential patch-clamp recordings in cell culture and in vivo.

These and other objects, features and advantages of the present invention will become more apparent upon reading the following specification in conjunction with the accompanying drawing figures.

BRIEF DESCRIPTION OF THE DRAWINGS

FIG. 2A shows a Scanning Electron Microscopy (SEM) image of a fresh pipette. FIG. 2B shows an SEM image of a pipette following a traditional patch-clamp trial. FIG. 2C shows an SEM image of a pipette following a traditional patch-clamp trial and a subsequent application of the cleaning method according to an exemplary embodiment of the present invention.

FIGS. 6(A-D) illustrate recording quality parameters $R_{GS}$, $T_{GS}$ and $R_a$ (whole-cell access resistance) (FIG. 6A). Pipette resistance before and after cleaning with Alconox (FIG. 6B). Change in pipette resistance from first to tenth re-use (FIG. 6C). Representative whole-cell responses to step current injections in different experimental preparations (FIG. 6D).

FIGS. 11(A-D) illustrate pipette cleaning in conjunction with $GABA_AR$ pharmacology. Representative current traces recorded by whole-cell patch-clamp recording of HEK293T cells transfected with αβ2γ2s $GABA_ARs$ (FIG. 11A). Representative normalized peak current responses to different GABA concentrations (FIG. 11B). Dose response characteristics of cells patched with fresh and re-used pipettes (FIG. 11C). That a low dose of Alconox (67 μg/mL, or equivalently, 385× the detection limit of remaining Alconox in the pipette after cleaning) in the internal solution does not affect dose response characteristics (FIG. 11D).

FIGS. 12(A-B) show a pipette containing a high dose (10 mg/mL) of Alconox damages the target cell during a patch attempt.

DETAILED DESCRIPTION OF THE INVENTION

Figure 1A:
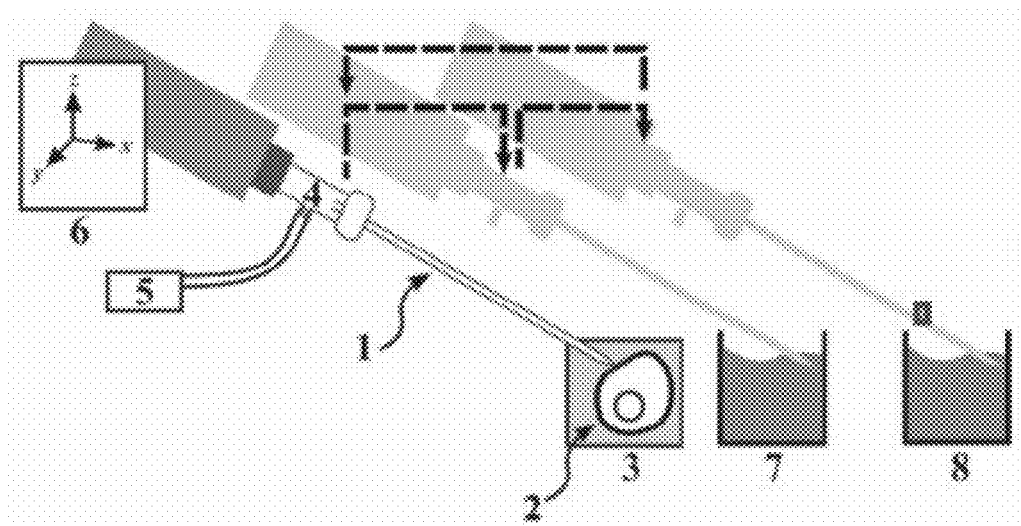
FIG. 1A is a schematic of a conventional patch-clamp, modified to enable the present process according to an exemplary embodiment.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

As shown in FIG. 1A, in an exemplary patch-clamp embodiment of the present invention, the distal end (an apertured surface) of a glass pipette 1 is attached to a single cell 2 in a preparation area 3. The pipette 1 is attached at the proximal end to a pipette holder 4. A cleaning solution chamber 7 containing a cleaning solution and a rinse solution chamber 8 containing a rinse solution are situated near the biological preparation area 3. Pressure is applied via a pressure controller 5 to the pipette 1 through the pipette holder 4. A three-axis micromanipulator 6 moves the pipette 1 and the pipette holder 4 in three dimensions.

Figure 1B:
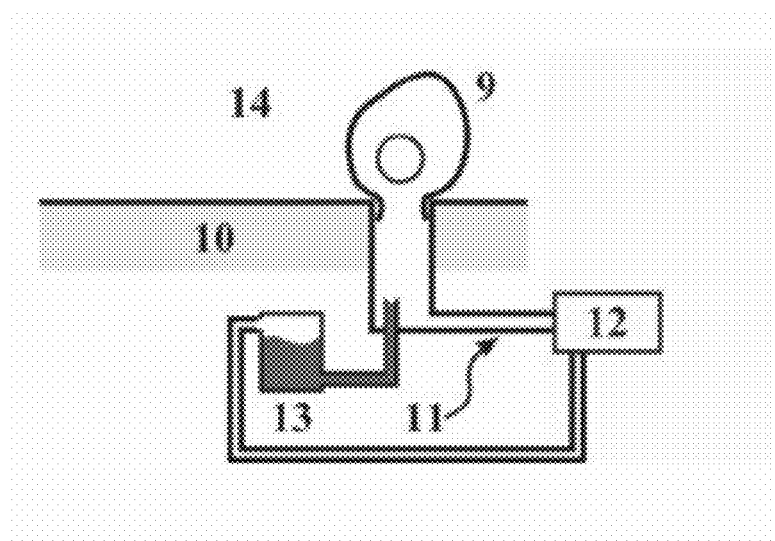
FIG. 1B is a schematic of a planar patch-clamp embodiment, modified to enable the present process according to an exemplary embodiment.

As shown in FIG. 1B, in a planar patch-clamp embodiment of the present invention, a cell 9 in an extracellular fluid medium 14 is sealed to (at an apertured surface of) a planar glass electrode 10 at the opening to the intracellular fluid space 11. Pressure is applied via one channel on a pressure controller 12. Cleaning fluid from cleaning fluid chamber 13 is dispensed into the intracellular fluid space 11 via another channel on the pressure controller 12.

In operation of the system of FIG. 1A, the micromanipulator 6 is used to bring the glass pipette 1 to the preparation area 3 to approach the single cell 2. Negative pressure is applied via the pressure controller 5 and the membrane of the cell 2 adheres to the distal end of the pipette 1.

Following an electrophysiological experiment, the micromanipulator 6 withdraws the pipette 1 from the cell 2 and expels large, adherent cellular debris from the pipette 1 with high positive pressure from the pressure controller 5. The micromanipulator 6 then moves the pipette 1, under high positive pressure via the pressure controller 5, from the preparation area 3 and into the chamber 7 containing cleaning solution. Pressure is then cycled a number of times between positive pressure and negative pressure with the pressure controller 5 to bring the cleaning solution within the chamber 7 into contact with the interior and exterior surfaces of the pipette 1 and to cyclically apply shear forces to the interior surface of the pipette 1. The micromanipulator 6 then moves the pipette 1, under high positive pressure from the pressure controller 5, from the chamber 7 containing cleaning solution into the chamber 8 containing rinse solution. Pressure is then cycled a number of times between positive pressure and negative pressure with the pressure controller 5 to bring the rinse solution within the chamber 8 into contact with the interior and exterior surfaces of the pipette 1 and to remove any residual cleaning solution from the interior and exterior surfaces of the pipette 1. The micromanipulator 6 then moves the pipette 1, under high positive pressure from the pressure controller 5, from the chamber containing rinse solution 8 and back to the preparation area 3. Subsequent electrophysiological trials can be performed by repeating the steps described above.

In operation of the system of FIG. 1B, the suspension containing one or more cells 9 in the extracellular fluid medium 14 is passed over an aperture in the planar glass electrode 10 leading to the channel 11 containing intracellular fluid. Suction is applied to the intracellular fluid space 11 via pressure controller 12 to draw the suspended cell 9 to the aperture and form a gigaseal.

Following the electrophysiological experiment, high pressure is applied to the intracellular space 11 via pressure controller 12 to eject the cell 9 and bulk cellular debris from the aperture. Pressure is applied to the cleaning solution channel 13 via pressure controller 12 to eject cleaning fluid into the intracellular space 11 and bring cleaning fluid into contact with the interior wall of the intracellular channel 11. Simultaneously, pressure is cycled between positive and negative pressure (suction) on the intracellular channel 11 a number of times to cyclically apply shear forces to the surface of intracellular channel 11. The cleaning solution channel 13 is then returned to atmospheric pressure or slight negative pressure via the pressure controller 12 to prevent excess cleaning solution from entering the intracellular space 11. Positive pressure is applied to the intracellular space 11 via pressure controller 12 to eject any remaining debris and residual cleaning chemical. Subsequent electrophysiological trials can be performed by repeating the steps described above.

FIGS. 2(A-C) are SEM images of pipette tips. FIG. 2A is an SEM image of a fresh pipette. FIG. 2B shows an SEM image of a pipette tip cleaned with aCSF and being visibly contaminated with cell membrane residue, illustrating the necessity of throwing out the conventional pipette after each use (it cannot be re-used without a viable cleaning and rinsing regime heretofore unknown). FIG. 2C is an SEM image of a pipette following the present inventive cleaning and rinsing regime (namely using Alconox), illustrating the capability of pipette re-use. The Alconox-cleaned pipette tip resembles that of the fresh pipette. Pipette filament denoted with *. Scale bar: 1 µm.

Figure 3:
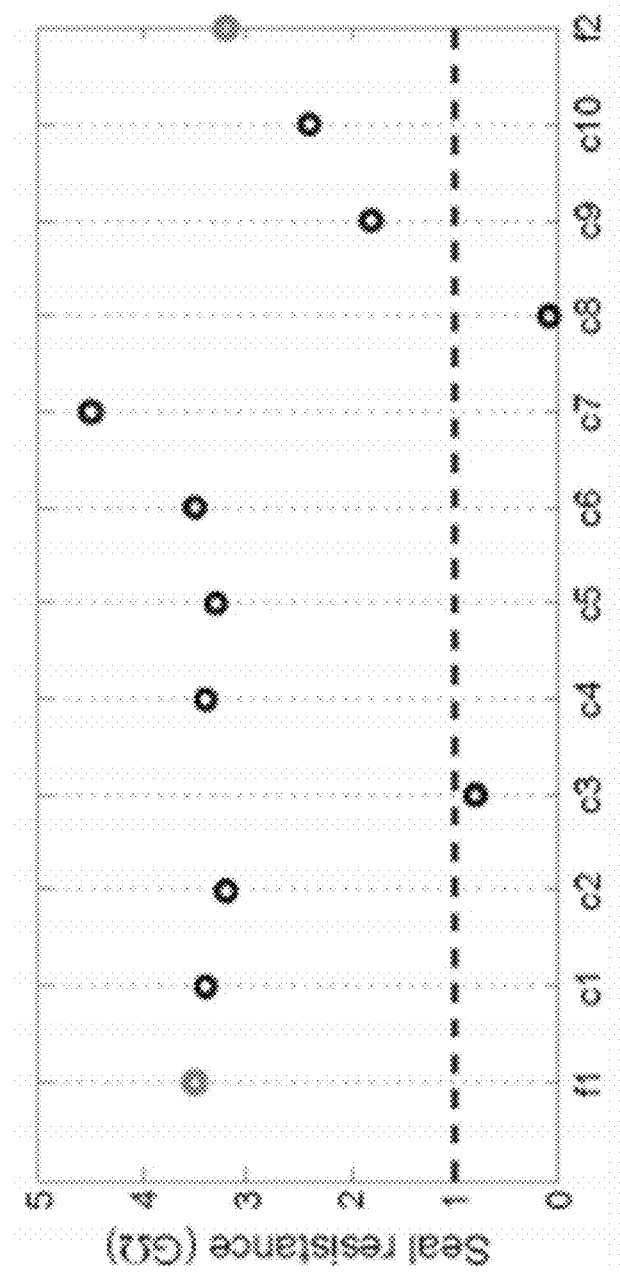
FIG. 3 is a graph of the gigaseal resistances of ten sequential patch-clamp trials using one pipette that was cleaned according to an exemplary embodiment of the present invention.

FIG. 3 illustrates the resulting gigaseal resistances of ten sequential patch-clamp trials using one pipette that was cleaned with the present method. In 8/10 trials, a gigaseal was successfully established.

In exemplary embodiments of the present invention shown in FIGS. 4-12, FIGS. 4(A-D) illustrate cleaning patch-clamp pipettes. During a whole-cell patch-clamp recording, cell membrane bonds to the inner walls of the pipette (FIG. 4A). After the recording is terminated, membrane residue remains, preventing the pipette from being used for subsequent recordings. (FIG. 4B) to clean, (i) the pipette is moved from the experimental preparation to a wash bath where a cleaning agent is cycled within the tip, (ii) then to a rinse bath where the remaining cleaning agent is expelled into aCSF, (iii) and returned back to the experimental preparation. (FIG. 4C) Representative gigaseal formation traces. When using contaminated pipettes cleaned with Alconox, a multi-GΩ seal forms reliably, as would be expected when using a fresh pipette. On the other hand, cleaning with aCSF and bleach does not result in gigaseal formation. $R_{GS}$: maximum gigaseal resistance, $T_{GS}$: time (s) to reach 1 GΩ (horizontal dashed line). (FIG. 4D). Of the six tested detergents and aCSF, only Alconox reliably achieved gigaseal resistances comparable to those of fresh pipettes (p<0.001; one-way ANOVA with Dunnett's post-hoc test. *: p<0.001; n.s.: not significant, p>0.9). Data shown as mean±s.d.; n for each cleaning agent is shown in parentheses. PLA2: Phospholipase A2; SDS: Sodium Dodecyl Sulfate.

Figure 4A:
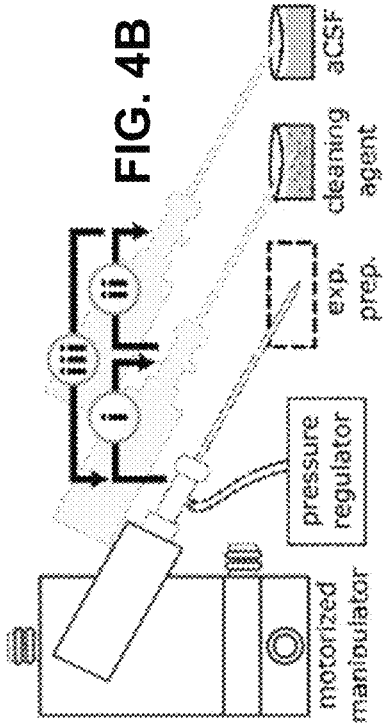
FIGS. 4(A-D) illustrate that during a whole-cell patch-clamp recording, cell membrane bonds to the inner walls of the pipette (FIG. 4A). A schematic of the present process according to an exemplary embodiment (FIG. 4B). Representative gigaseal formation traces (FIG. 4C). Representative resistances (FIG. 4D).
Figure 4B:
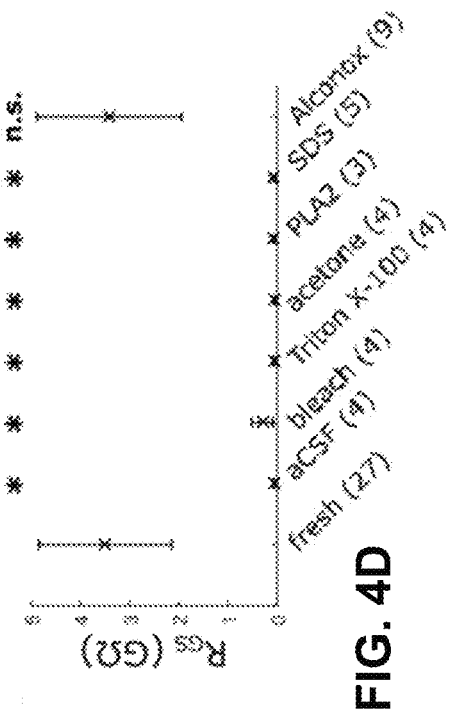
Figure 4C:
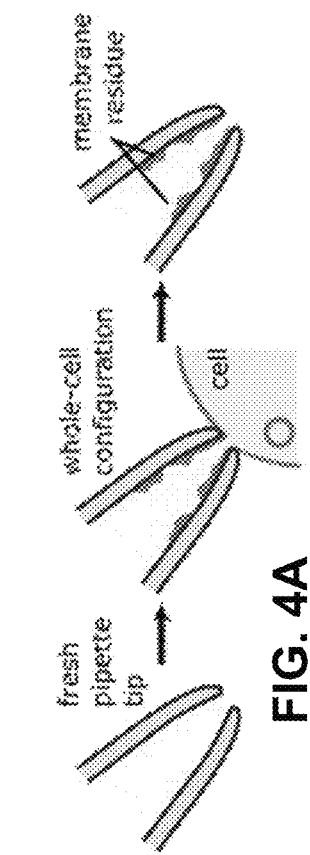
Figure 4D:
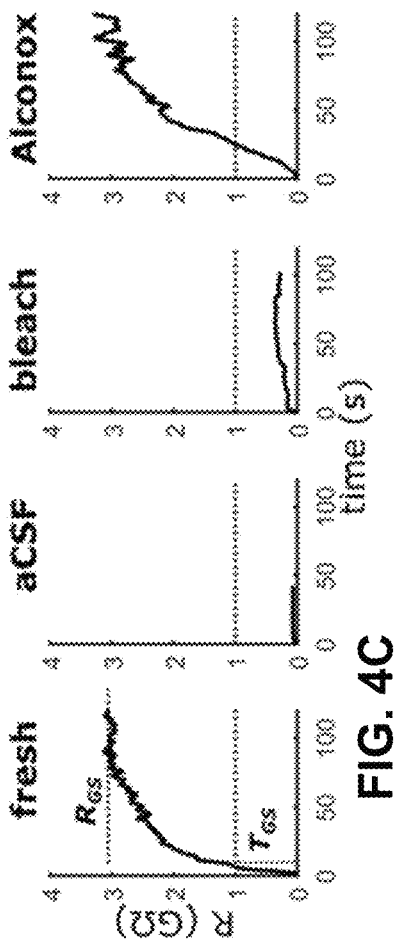

As discussed above, during a whole-cell patch-clamp recording (FIG. 4A), cell membrane bonds to the inner walls of the pipette. After the recording is terminated, membrane residue remains, preventing the pipette from being used for subsequent recordings. After a recording attempt in an experimental preparation, pipette cleaning is accomplished in three steps (FIG. 4B). First, the pipette is moved to a bath containing a cleaning agent. Using an electronic pressure regulator, a series of alternating negative and positive pressures is applied to the pipette to cycle the cleaning agent within the tip.

Second, the pipette is moved to a bath containing aCSF. Using another series of pressure pulses, any remaining cleaning agent in the pipette is expelled. Based on the calculated fluid flow rates from pipettes (~3 nL/s, based on pipette inner diameter of 1 μm), this pressure series is sufficient to intake the cleaning agent at least 200 μm into the lumen of the pipette. This exceeds the height of a typical lipid 'bleb' that forms in the pipette tip during a gigaseal (30-60 μm).

Lastly, the pipette is moved back to the experimental preparation. Pipettes can then be immediately re-used for a subsequent patch-clamp attempt. Refilling a pipette with internal solution is unnecessary because pipettes are commonly filled with enough solution for hundreds of attempts. All moving and cleaning steps together require 60 seconds.

TABLE 1

| Cleaning solution | Source |
|---|---|
| Bleach (8.25% Sodium hypochlorite) | The Clorox Company |
| Triton X-100 | X100-5 mL (Sigma-Aldrich) |
| Acetone | BDH1101 (VWR) |
| Phosopolipase A₂ (PLA, 0.0001% w/v in 10 mM HEPES buffer) | P7778 (Sigma-Aldrich) |
| Sodium Dodecylbenzenesulfonate (SDS, 1% w/v) | TCD0990 (VWR) |
| Alconox (2% w/v) | Alconox Inc. |

Alconox was one cleaning agent that enabled pipettes to be re-used in quantities sought. Whole-cell patch-clamp recordings on human embryonic kidney (HEK293T) cells were performed using fresh (previously unused) pipettes, cleaned them with one of six different commonly available glassware cleaning agents as shown in TABLE 1, as well as a control solution (aCSF), and attempted to patch another cell with the same pipette. On the second attempt, pipettes cleaned with Alconox, but not with any other cleaning agent, produced gigaseal resistances ($R_{GS}$) that were not significantly different from those produced by fresh pipettes (FIGS. 4(C)(D)). Successful whole-cell recording rates were not different between fresh and Alconox-cleaned pipettes (fresh=92.6%, Alconox-cleaned=88.9%, p=0.87, Fisher's exact test; other detergents and aCSF=0%).

Figure 5:
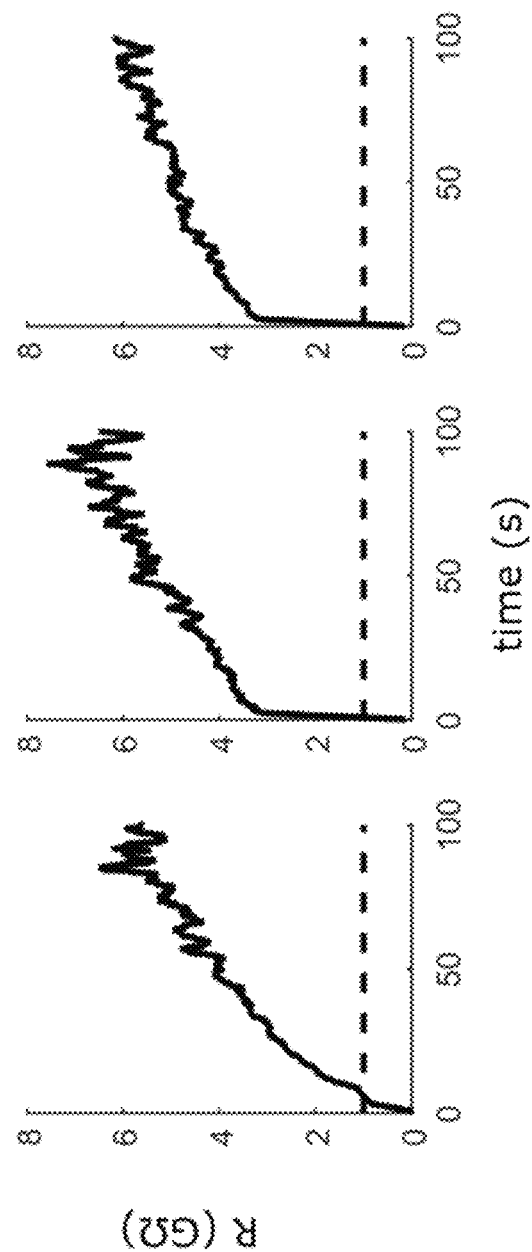
FIG. 5 presents three representative gigaseals obtained with fresh pipettes that were pre-cleaned in Alconox. Pre-cleaning did not hinder the formation of stable gigaseals.

Gigaseals were held for 1-2 minutes to ensure stability. No gigaseals were spontaneously lost during this time in either fresh or Alconox-cleaned pipettes. When using Alconox-cleaned pipettes, an outside-out patch reliably formed after withdrawing the pipette from the cell, as would be expected if using fresh pipettes. Further, pre-cleaning fresh pipettes in Alconox had no effect on gigaseal formation. FIG. 5 presents three representative gigaseals obtained with fresh pipettes that were pre-cleaned in Alconox. Pre-cleaning did not hinder the formation of stable gigaseals.

Using SEM, the tip of the pipettes was confirmed as being cleaned using Alconox but not aCSF (FIGS. 2(A-C)). Unless stated otherwise, all subsequent experiments used Alconox.

FIGS. 6(A-D) illustrate that pipettes can be successfully re-used ten times. (FIG. 6A) Recording quality parameters $R_{GS}$, $T_{GS}$ (defined in FIG. 4C) and $R_a$ (whole-cell access resistance) do not decrease over ten re-uses of the same pipette (n=8 pipettes). Dashed line: 1 GΩ (threshold for gigaseal). Gray circles: individual trials; black circles: representative experiment with a single pipette. Data shown as mean±s.d. (FIG. 6B) Pipette resistance before and after cleaning with Alconox (n=88 pairs, 8 pipettes). (FIG. 6C) Change in pipette resistance from first to tenth re-use. After ten re-uses, resistance changed (ΔR) by median: 0.175 MΩ, max: 0.61 MΩ, min: −0.44 MΩ from fresh pipette. (FIG. 6D) Representative whole-cell responses to step current injections in different experimental preparations. Recordings from HEK293T cells were obtained from the representative experiment (black circles) in (FIG. 6A). In each set, a single pipette is used for all three whole-cell recordings. In all preparations pipettes were re-used up to ten times.

As discussed above, pipettes could be re-used ten times consecutively with little to no degradation in recording quality if they were cleaned between each patch-clamp attempt (FIG. 6A). 84 HEK293T cells were successfully patched (of n=88 attempts including one fresh and 10 ten; success rate=95%) using eight pipettes, and found no effect of the number of re-uses on gigaseal resistance ($R_{GS}$), the time to reach 1 GΩ ($T_{GS}$), and the access resistance of the patched cell ($R_a$) for each trial (one-way repeated-measures ANOVA with number of re-uses (1-10) as predictor; $R_{GS}$: $F_{10,40}$=0.99, p=0.46, n=8; $T_{GS}$: $F_{10,40}$=0.36, p=0.96, n=5, $R_a$: $F_{10,40}$=0.72, p=0.70, n=5).

Notably, even when pipettes failed to reach a gigaseal (e.g., $R_{GS}$<1 GΩ on third, fourth re-use in FIG. 6A), they were successfully cleaned and re-used again, suggesting that gigaseal failures did not irreversibly contaminate the pipette tip. Beyond ten re-uses were not tested to perform a systematic study of pipette longevity; however, a pilot experiment confirmed the suspicion that pipettes could not be re-used indefinitely, when three consecutive failed patch-clamp attempts occurred after 26 re-uses.

Figure 7:
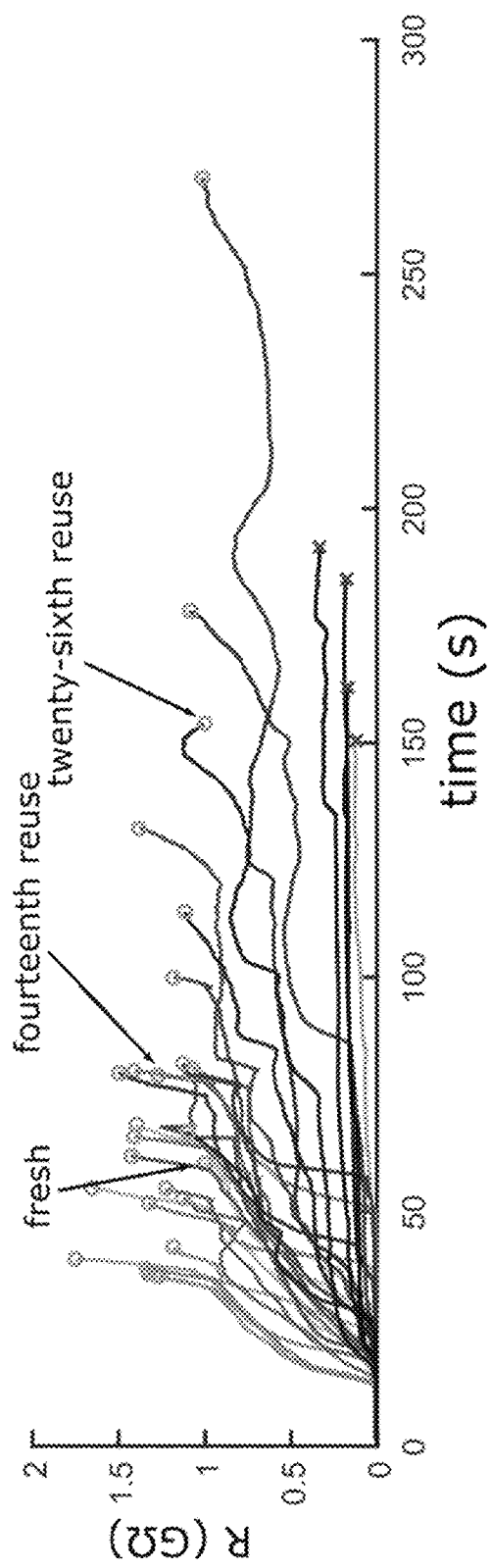
FIG. 7 is a graph of gigaseal resistances of thirty re-use attempts with a single pipette over time.

FIG. 7 illustrates the gigaseal resistances of thirty re-use attempts with a single pipette. The pipette was successfully re-used twenty-six times (green circles: R>1 GΩ). The pipette did not reach a gigaseal on the fifth re-use, and consecutively on twenty-seventh through thirtieth re-use (circles: R<1 GΩ). Gigaseal attempts are coded from light to dark according to the number of times the pipette was used. After approximately fourteen re-uses, the time to form a gigaseal increases.

The patency of the pipette tip is commonly assessed during patch-clamp recording by measuring its electrical resistance. To assess whether cleaning reduced the amount of contamination on the pipette tip, the resistance was measured twice: once immediately after completing a whole-cell recording (before cleaning) and once more after cleaning. As expected, pipette resistance before cleaning was higher than after (FIG. 6B; before: median=5.93 MΩ, range: 4.49 to 15.0 MΩ; after: median=5.77 MΩ, range=4.46 to 6.28 MΩ; p<0.05, Wilcoxon signed-rank test). Over 10 re-uses, the resistance of the pipette did not change significantly (FIG. 6C); p≥0.19 for first-tenth re-use, n=8, Wilcoxon signed-rank test). Together, these results suggest that cleaning eliminates residue obstructions on the pipette tip over ten re-uses.

Repeated patch-clamping in neuron cultures, acute brain slices, and in vivo were done using a single pipette for each experimental preparation (FIG. 6D). Cleaning did not visibly alter action potential generation in these experiments. In brain slices, successful gigaseals and successful whole-cell recordings were attained at similar rates between fresh and cleaned pipettes (gigaseals: fresh=78%, cleaned=82%, p=0.73; whole-cell recordings: fresh=39%, cleaned=48%, p=0.58, Fisher's exact test).

Figure 8:
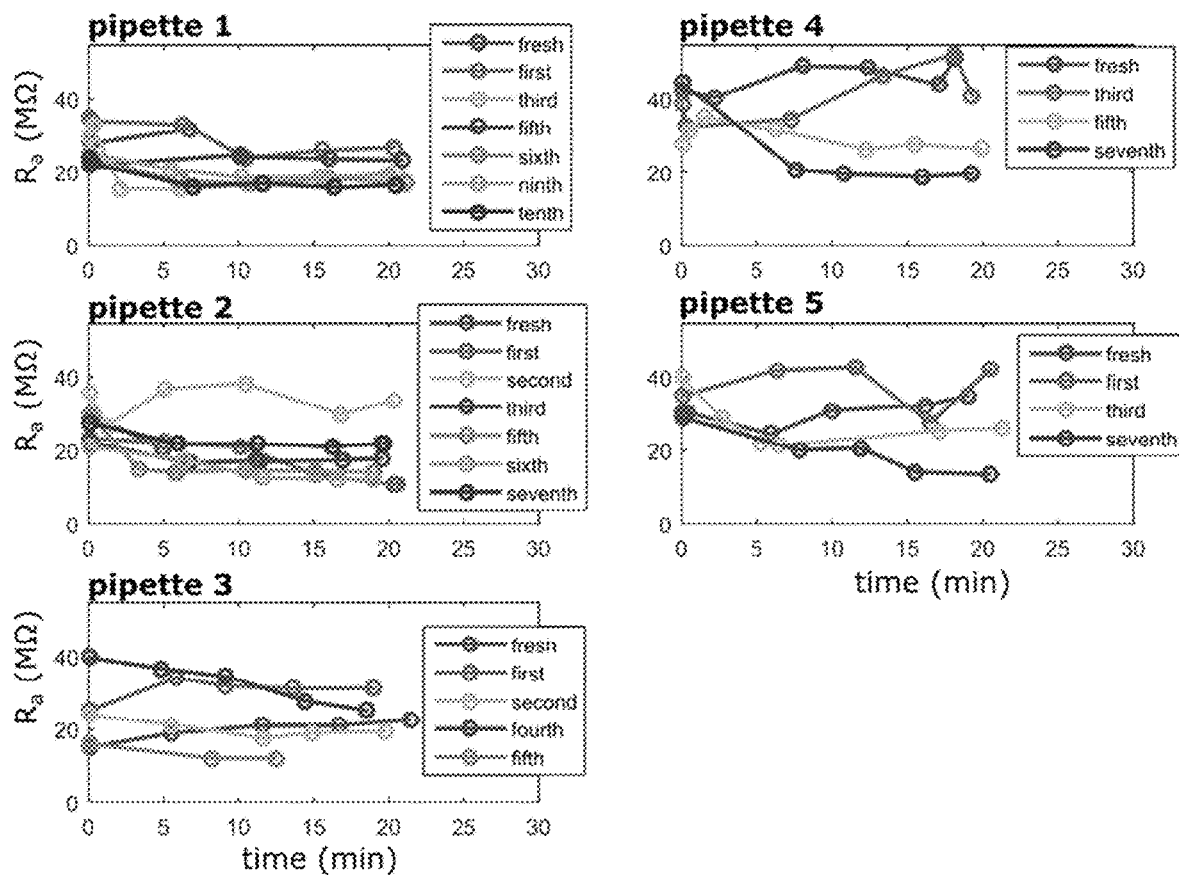
FIG. 8 illustrates graphs for five pipettes wherein successful attempts resulting in whole-cell recordings are shown.

As shown in FIG. 8, in slices, neurons were recorded and found to have the access resistance stable across that time, indicating that whole-cell recordings obtained using cleaned pipettes are stable over the duration of a typical experiment. For each plot, a single pipette was used. Only successful attempts (resulting in whole-cell recordings) are shown. Cells were held for ~20 minutes. Access resistance did not increase for fresh pipettes as well as for pipettes re-used 1-10 times, indicating stable whole-cell recordings. In vivo, the Autopatcher was used to patch-clamp repeatedly with the same pipette in mouse barrel cortex (depths: 400-600 um).

Verifying Detergent Removal after Pipette Cleaning

A major concern of using any detergent to clean pipettes is that residual surfactants in the pipette could damage the cell or affect its normal biophysical activity during a cell-attached or whole-cell patch-clamp recording. For example, Alconox comprises 33-43% sodium bicarbonate, 10-20% sodium (C10-C16) LAS, 5-15% sodium tripolyphosphate, 5-15% tetrasodium pyrophosphate, 1-10% sodium carbonate, and 1-5% sodium alcohol sulfate. LAS was chosen, a commonly-used surfactant, as a proxy for measuring Alconox concentration remaining after rinsing.

Figure 9A:
FIG. 9A illustrates the chemical formula for sodium (C10-C16) linear alkylbenzene sulfonate (LAS). How the contents of cleaned pipettes were collected in vials (FIG. 9B). ESI-MS spectrum (FIG. 9C).
Figure 9B:
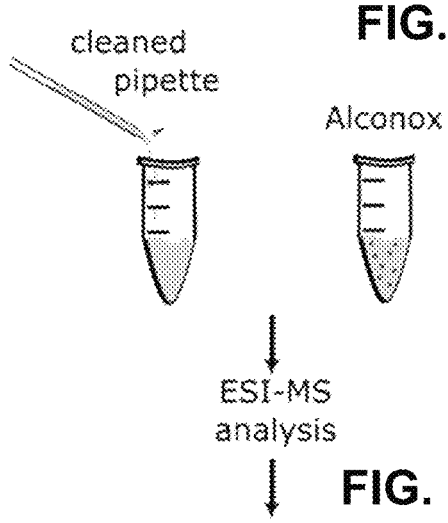
FIGS. 9(A-C) illustrate that LAS is the prevalent cytotoxic ingredient in Alconox.
Figure 9C:
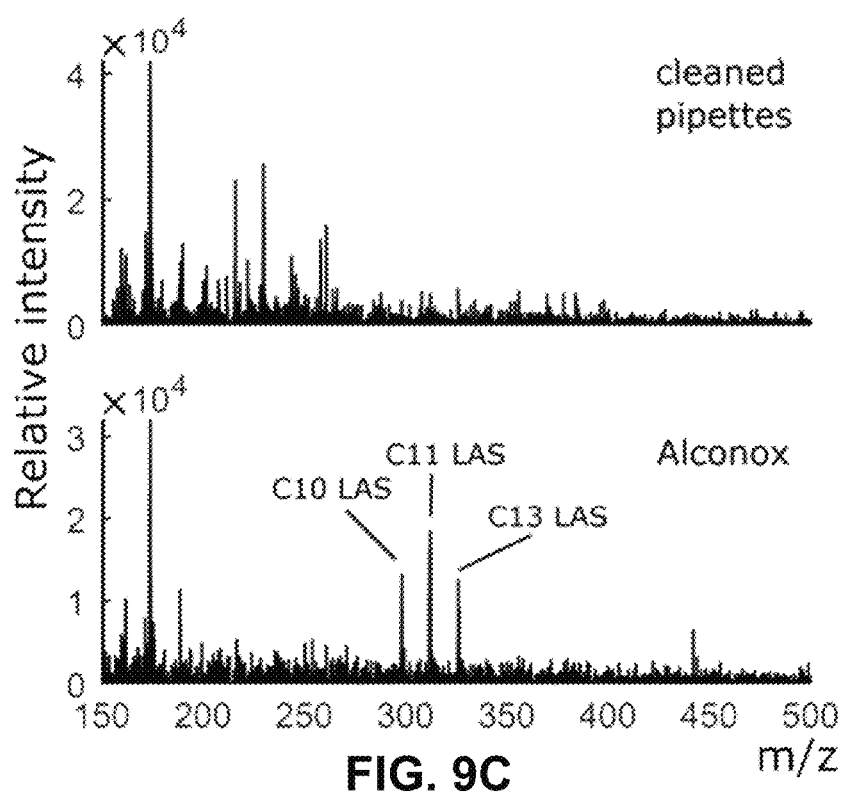

FIGS. 9(A-C) illustrate detection of LAS in cleaned pipettes using electrospray ionization mass spectrometry (ESI-MS). (FIG. 9A) LAS is the prevalent cytotoxic ingredient in Alconox.

Alconox is composed of LAS with carbon chains lengths 10-12 (C10-C12). (FIG. 9B) The contents of cleaned pipettes were collected in vials. Known amounts of Alconox were analyzed to find the detection limit. (FIG. 9C) ESI-MS spectrum. C10-C12 LAS is not detectable in cleaned pipettes (top) but is detected in a defined Alconox solution (174 ng/mL Alconox in DI water, bottom), indicating that less than 174 ng/mL of Alconox remains in the pipettes after cleaning. C10: expected m/z: 297.1, found: 297.3; C11: expected m/z: 311.2, found: 311.2; C12: expected m/z: 325.2, found: 325.1.

Figure 10:
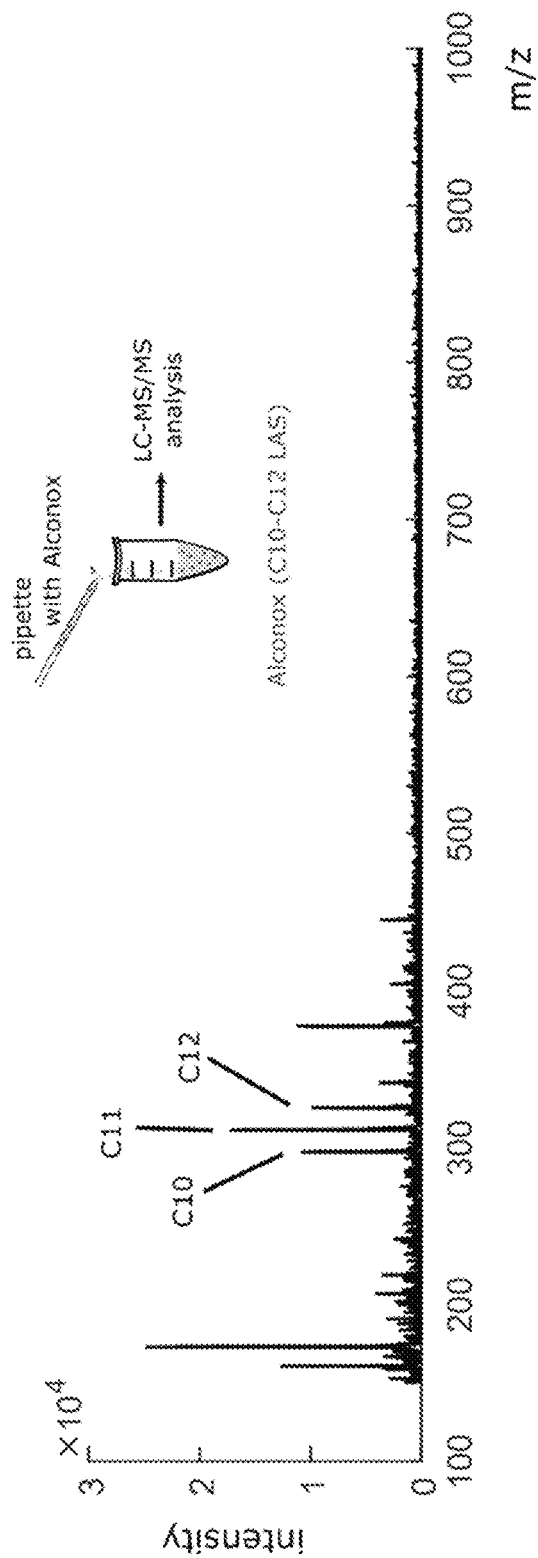
FIG. 10 is a schematic ESI-MS spectrum characterization of pipettes containing 67 μg/ml Alconox dissolved in DI water. The main cytotoxic components of Alconox, C10-C12 LAS compounds were identified in the solution (C10: expected m/z: 297.1, found: 297.1; C11: expected m/z: 311.2, found: 311.1; C12: expected m/z: 325.2, found: 325.2).
Figures 12A, 12B:
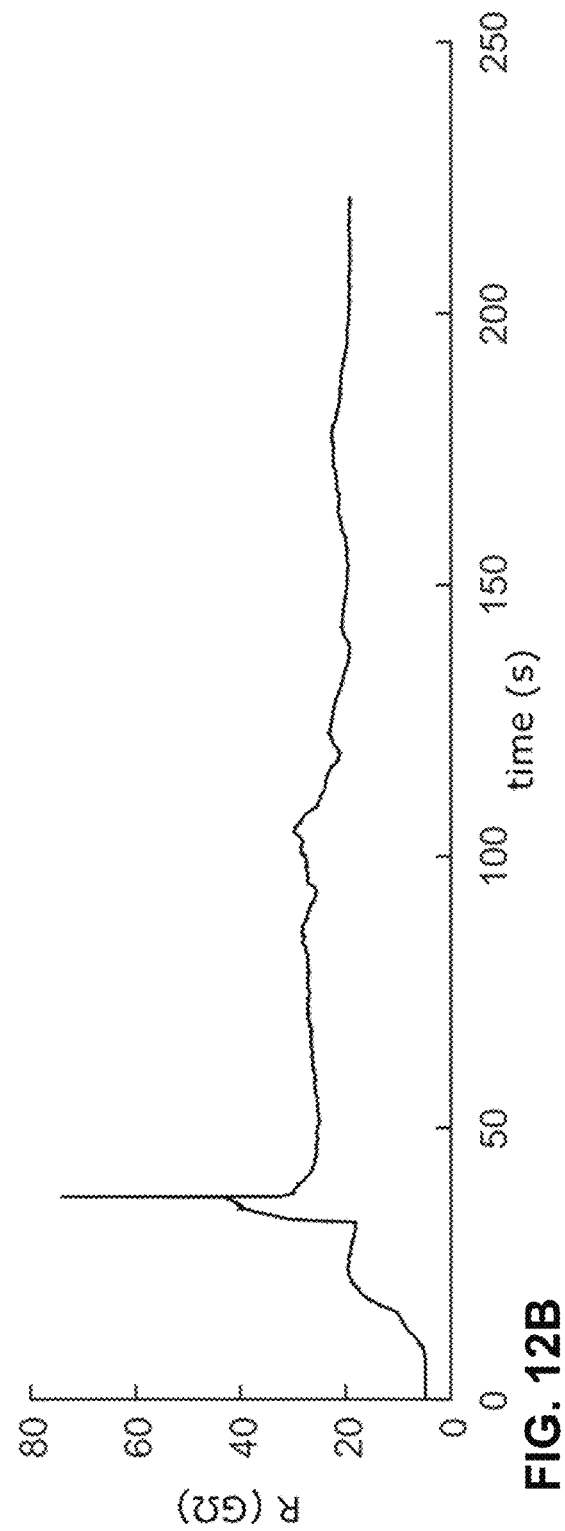
(FIG. 12A) A gigaseal fails to form after >3 min, suggesting that Alconox is destroying cell membrane.
(FIG. 12B) Cell apoptosis during the gigaseal process is evident. Arrow indicates blebs forming on the cell. Scale bar: 10 μm.

As discussed above, the amount of Alconox remaining after cleaning was measured using electrospray ionization mass spectrometry (ESI-MS). As shown in FIG. 10, only C10-C12 LAS was found in significant quantities in the Alconox solution, so the analysis was focused on this family of compounds (FIG. 9A). No traces of LAS was found in cleaned pipettes (FIG. 9(B), (C) (top)), while the instrumentation detection limit was found to be 174 ng/mL (FIG. 9C (bottom)). Thus, less than 174 ng/mL of Alconox remained in the pipettes after the cleaning procedure. As a control, as shown in FIG. 10, LAS was ensured it could still be detected using ESI-MS when purposefully introduced in small concentrations into the pipette.

Any effect of trace amounts of Alconox in cleaned pipettes on cell receptor pharmacology would be highly undesirable. Residual LAS could disrupt gigaseal formation, thus decreasing signal quality or, more subtly, interact with amphipathic allosteric modulatory pockets on receptors, thus covertly compromising pharmacological experiments. The γ-aminobutyric acid type A Receptor ($GABA_AR$) is highly sensitive to extracellular application of surfactants, including LAS; its intracellular effects have not been thoroughly studied. Nevertheless, it is reasoned that $GABA_AR$ could serve as an indicator of adverse effects of Alconox.

FIGS. 11(A-D) illustrate pipette cleaning in conjunction with $GABA_AR$ pharmacology. (FIG. 11A) Representative current traces recorded by whole-cell patch-clamp recording of HEK293T cells transfected with α1β2γ2s $GABA_A$Rs. Black bar denotes GABA application (FIG. 11B) Representative normalized peak current responses to different GABA concentrations.

The response captured with a fresh pipette is similar to that captured with a used pipette (fourth re-use). (FIG. 11C) Dose response characteristics of cells patched with fresh and re-used pipettes. $i_{pk}$: peak evoked current; h: Hill coefficient; $EC_{50}$: half-maximal response concentration. No change in the three characteristics is observed over four re-uses. (FIG. 11D) A low dose of Alconox (67 μg/mL, or equivalently, 385× the detection limit of remaining Alconox in the pipette after cleaning) in the internal solution does not affect dose response characteristics.

As discussed above, HEK293T cells expressing $GABA_AR$ were used as a model system to verify that cleaned pipettes are pharmacologically inert. Patch-clamping using fresh and cleaned pipettes was performed, and fit the measured whole-cell current responses to increasing concentrations of GABA (FIG. 11A) to the Hill equation. Neither the peak evoked current ($I_{pk}$), the Hill's coefficient (h), nor the half maximal effective concentration ($EC_{50}$) metrics changed as a function of re-uses (linear regression model, $H_0$: slope≠0; $I_{pk}$: p=0.998, 95% CI: −318 to 317 pA; h: p=0.719, 95% CI: −0.065 to 0.093; $EC_{50}$: p=0.751, 95% CI: −6.75 to 4.90).

This finding demonstrates that GABA concentration-response curves of the patch-clamped cells do not change on a population level as a function of the number of times a pipette has been re-used (FIGS. 11(B), (C)). Overall, pharmacology results obtained using fresh pipettes were indistinguishable from those obtained using cleaned pipettes, suggesting no effect of trace amounts of Alconox on normal receptor function of $GABA_A$Rs.

It was also found that even if small amounts of Alconox remain in the pipette after cleaning, they do not impact gigaseal formation or $GABA_AR$ pharmacology. When 67 μg/mL of Alconox (385× the ESI-MS detection limit) was intentionally dissolved in the pipette internal solution, gigaseals were still reliably achieved in all tested pipettes (n=9). No pharmacological difference between these pipettes and fresh ones was detected (FIG. 11D; $I_{pk}$: p=0.37; h: p=0.99;

EC$_{50}$: p=0.19). On the other hand, when a much larger dose, 10 mg/mL Alconox (0.5× the concentration in the wash bath) was added to the pipette, gigaseals did not form and the targeted cell exhibited clear apoptotic blebbing. See, FIGS. 12(A-B).

Unattended, Sequential Patch-Clamp Recording

Previous efforts have partially or fully automated the process of obtaining a single whole-cell recording in vitro as well as in vivo; however, in all of these studies, a trained user was needed to exchange pipettes to start another attempt. Removing this manual step would enable unattended patch-clamp experiments and improve scalability and throughput. To explore this, the pipette cleaning algorithm was integrated into the previously-developed Autopatcher software. The resulting robot was tested, which was called 'patcherBot' by first performing patch-clamp recordings in HEK293T cells.

After the user selected candidate cells for patch-clamp recording, the patcherBot obtained successful gigaseals in 9/10 attempts, and successful whole-cell recordings in 6/10 attempts over the span of 33 minutes of unattended operation using a single pipette. The patcherBot was also deployed to perform blind, in vivo patch-clamp recordings in the mouse barrel cortex. Using four pipettes, the robot obtained successful gigaseals in 13/34 attempts, and successful whole-cell recordings in 10/34 attempts over a total span of 171 minutes in vivo (FIG. 6D).

Discussion

Discovering that pipettes could be reliably cleaned and re-used multiple times was surprising given the dogmatic, decades-long practice of replacing pipettes after each patch-clamp attempt. The present simple, fast, and automated procedure comprises dipping pipettes into a commercially-available detergent, Alconox, followed by rinsing in aCSF. It is herein demonstrated the effectiveness of this cleaning method by re-using pipettes ten times, with no decrease in whole-cell recording quality in cultured cells, acute brain slices, and in vivo. After cleaning, the residual Alconox mass concentration in the pipettes was quantified to be less than 174 ng/mL, and shown to have no pharmacological effect on GABA$_A$Rs. Since pipette cleaning is automatic, it was integrated into the Autopatcher to perform unattended, sequential patch-clamp recordings on HEK293T cells in vitro and neurons in vivo.

Alconox is composed of a surfactant, emulsifier and water softener, and in solution, it interacts with cell membranes bound to the glass pipette tip. These three ingredients solubilize adhered lipids, stabilize the lipid micelles in solution, and enhance surfactant effectiveness, respectively. After testing various cleaning agents, it was not evident why only Alconox sufficiently cleaned pipettes to enable their re-use. Interestingly, prior studies used bleach to successfully clean planar borosilicate patch-clamp chips up to five times for whole-cell recording; yet in the present experiments using conventional pipettes, bleach did not work, suggesting that the geometry of the experimental preparation may influence cleaning effectiveness.

Overall, the precise mechanism of how cell membranes bond with glass during a gigaseal is still not understood despite notable efforts, making it difficult to devise a cleaning strategy from basic principles. A detailed biochemical study of gigaseal formation could therefore greatly inform efforts to optimize cleaning, and potentially increase the number of re-uses.

While it has herein been demonstrated that cleaning does not affect the ion channel pharmacology of GABA$_A$Rs, it was not exhaustively tested that the method in cells expressing other proteins. While several studies have characterized the effects of extracellularly applied detergents on various receptors, the intracellular effect of LAS in small concentrations is not well-understood. Thus to verify general applicability, the method should be validated using more channels, receptors, and cell types.

For many patch-clamp experiments, pipette internal solution contains ingredients that degrade over time if not refrigerated (e.g. Adenosine 5'-triphosphate magnesium salt, Guanosine 5'-triphosphate sodium salt hydrate, phosphocreatine); thus, it is expected that pipettes after multiple cleanings will have reduced concentrations of these ingredients. It is hypothesized that maintaining a chilled (i.e., 4° C.) environment for pipette and internal solution, or devising a method for replacing internal solution after every trial could mitigate this deleterious effect.

The cleaning process is typically faster than manually swapping pipettes (i.e., one minute versus approximately two minutes) and does not depend on operator experience, dexterity, or fatigue level. It requires no complex hardware additions to existing electrophysiology setups and no expensive or caustic reagents. Therefore, it can be readily integrated into different experimental preparations and coupled with existing techniques that complement patch-clamp such as extracellular stimulation, two-photon microscopy, and optogenetics.

Pipette cleaning also facilitates experiments requiring specialized pipette tips. Various tip polishing techniques (using heat, pressure, or focused ion beam) and coatings can improve the ability to obtain recordings and their quality; however, these techniques are typically too time-consuming to be routine. The ability to re-use these custom-shaped pipettes could make these involved techniques more practical and scalable, reducing the need for automated pipette fabrication and inspection.

Further, the need for trained users to manually exchange pipettes is still a barrier to large-scale patch-clamp studies in the brain. In creating the patcherBot, the first robot to successfully patch-clamp multiple cells without human intervention was demonstrated. In addition to automation, cleaning could also greatly facilitate simultaneous multi-patch (i.e. dual, quadruple, octuple, etc.) experiments that have been instrumental in elucidating single-cell connectivity patterns in the brain. Since cleaning is faster than manual pipette exchange and requires no human intervention, it could increase the number and duration of simultaneous recordings.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. A method of detecting one or more characteristics of cells comprising:
   forming a resistance seal of ≥1 GΩ with a membrane of a cell located in a preparation area with an apertured surface;
   preparing the apertured surface by:

moving the apertured surface from the location of forming the resistance seal to a cleaning chamber;

cleaning the apertured surface with cleaning solution in the cleaning chamber via a cleaning cycle of alternating positive and negative pressures to draw toward and expel from the aperture surface at least a portion of cleaning solution, wherein the cleaning cycle comprises −200 mbar for 10 seconds and 200 mbar for 30 seconds;

moving the apertured surface from the cleaning chamber to a rinsing chamber; and rinsing the apertured surface with rinse solution comprising an artificial cerebrospinal fluid (aCSF) solution in the rinsing chamber via a rinsing cycle of alternating positive and negative pressures to draw toward and expel from the aperture surface at least a portion of rinse solution, wherein the rinsing cycle comprises −200 mbar for 10 seconds and 200 mbar for 30 seconds; and forming a resistance seal of ≥1 GΩ with a membrane of a different cell located in the preparation area with the apertured surface;

wherein preparing the apertured surface enables re-use of at least portions of the same apertured surface with at least six different cells.

2. A system for detecting one or more characteristics of cells comprising:

an apertured surface configured to form a resistance seal with a membrane of a cell in a preparation area;

a re-use assembly comprising:

a cleaning chamber configured to contain cleaning solution;

a rinsing chamber configured to contain rinse solution; and a pressure assembly in communication with the aperture surface configured to provide alternating positive and negative pressures of up to ±1,500 mbar relative to atmosphere to draw toward and expel from the aperture surface at least a portion of cleaning solution and at least a portion of rinse solution; and an assembly in communication with the apertured surface and providing each resistance seal with a resistance of ≥1 GΩ;

wherein the re-use assembly prepares at least portions of the same apertured surface so it can be re-used to form a resistance seal with a membrane of at least six different cells via a re-use protocol configured to:

move the apertured surface to the cleaning chamber;

cycle a cleaning solution in and out of the apertured surface, each cycle comprising −200 mbar for 10 seconds and 200 mbar for 30 seconds;

move the apertured surface to the rinsing chamber; and expose the apertured surface to a rinse solution comprising aCSF at −200 mbar for 10 seconds and 200 mbar for 30 seconds.

3. The method of claim 1, wherein the apertured surface comprises the aperture of a pipette.

4. The method of claim 1, wherein cleaning the apertured surface enables re-use of at least portions of the same apertured surface with at least nine different cells within 33 minutes.

5. The method of claim 1, wherein the cleaning solution comprises a non-bleach detergent.

6. The method of claim 1, wherein the apertured surface comprises the aperture of a pipette;

wherein the rinsing cycle further comprises cycling the rinse solution at least 200 μm into a lumen of the pipette; and wherein a characteristic of the cells is selected from the group consisting of an electrical activity, a molecular activity, a drug screening property, cell type, a biophysical property, a morphological property and a genetic property.

7. The system of claim 2, wherein the cleaning solution comprises sodium bicarbonate, sodium (C10-C16) linear alkylbenzene sulfonate (LAS), sodium tripolyphosphate, tetrasodium pyrophosphate, sodium carbonate, and sodium alcohol sulfate dissolved in deionized water.

8. The system of claim 2, wherein the re-use assembly prepares at least portions of the apertured surface so it can be re-used to form a resistance seal with a membrane of at least seven different cells.

9. The system of claim 2, wherein the apertured surface comprises the aperture of a pipette.

10. The system of claim 2 further comprising an automated manipulator capable of moving the apertured surface between the preparation area, the cleaning chamber, and the rinsing chamber by the agency of an automated process.

11. The system of claim 2, wherein the system is configured to clean the apertured surface with cleaning solution from the cleaning chamber in one minute or less.

12. The system of claim 2, wherein the re-use assembly prepares at least portions of the apertured surface so it can be re-used to form a resistance seal with a membrane of at least nine different cells within 33 minutes.

13. A method of detecting one or more characteristics of cells comprising:

forming a resistance seal of ≥1 GΩ with a membrane of a cell located in a preparation area with an aperture of a pipette;

preparing the aperture of the pipette in one minute or less comprising:

moving the aperture of the pipette from the preparation area to a cleaning chamber;

cleaning the aperture of the pipette with cleaning solution in the cleaning chamber using an electronic pressure regulator to provide a series of alternating negative and positive pressures to the aperture of the pipette to cycle the cleaning solution;

moving the aperture of the pipette from the cleaning chamber to a rinsing chamber; and rinsing the aperture of the pipette with rinse solution in the rinsing chamber, the rinse solution comprising artificial cerebrospinal fluid (aCSF), and rinsing comprising using the electronic pressure regulator to provide a series of alternating negative and positive pressures to the aperture of the pipette to cycle the rinsing solution at least 200 μm into a lumen of the pipette; and forming a resistance seal of ≥1 GΩ with a membrane of a different cell with the aperture of the same pipette;

wherein preparing the aperture of the pipette enables re-use of at least portions of the same pipette with at least six different cells.

14. The method of claim 13, wherein the aperture of the pipette has a diameter between 0.5-10 μm.

15. The method of claim 13, wherein the cleaning solution comprises a non-bleach detergent.

16. The method of claim 13, wherein the cleaning solution comprises a homogeneous blend of sodium linear alkylaryl sulfonate, alcohol sulfate, phosphates, and carbonates.

17. The method of claim 13, wherein cleaning solution comprises 33-43% sodium bicarbonate, 10-20% sodium (C10-C16) linear alkylbenzene sulfonate, 5-15% sodium tripolyphosphate, 5-15% tetrasodium pyrophosphate, 1-10% sodium carbonate, and 1-5% sodium alcohol sulfate.

18. The method of claim 13, wherein preparing the aperture of the pipette comprises preparing the aperture of the pipette by the agency of an automated process.

19. The method of claim 13, wherein at least portions of the aperture of the same pipette forms a resistance seal with a membrane of at least seven different cells.

20. The method of claim 13, wherein preparing the aperture of the pipette occurs in-between each step of forming a resistance seal with a membrane of a cell.

21. The method of claim 13, wherein cleaning the aperture of the pipette comprises subjecting the aperture of the pipette to a cleaning solution comprising an enzyme.

22. The method of claim 13, wherein a characteristic of the cells is selected from the group consisting of an electrical activity, a molecular activity, a drug screening property, cell type, a biophysical property, a morphological property and a genetic property.

23. The method of claim 13, wherein preparing the aperture of the pipette enables re-use of at least portions of the same pipette with at least nine different cells within 33 minutes.

24. A method of detecting one or more characteristics of cells comprising:
   forming a resistance seal with a membrane of a cell with an apertured surface;
   forming a resistance seal with a membrane of a different cell with the apertured surface; and
   preparing the apertured surface comprising:
      first rinsing the apertured surface with a rinse solution comprising a biological buffer via alternating positive and negative pressures using an electronic pressure regulator to draw the rinse solution at least 200 µm into a lumen of the apertured surface and expel the rinse solution from the aperture surface;
      after first rinsing, cleaning the apertured surface with a cleaning solution via alternating positive and negative pressures of up to ±1,500 mbar relative to atmosphere to draw toward and expel from the aperture surface at least a portion of the cleaning solution; and
      after cleaning, second rinsing the apertured surface with the rinse solution via alternating positive and negative pressures using the electronic pressure regulator to draw the rinse solution at least 200 µm into the lumen of the apertured surface and expel the rinse solution from the aperture surface;
   wherein preparing the apertured surface enables re-use of at least portions of the same apertured surface with different cells.

25. The method of claim 24, wherein the biological buffer comprises artificial cerebrospinal fluid (aCSF).

26. The method of claim 24, wherein preparing the apertured surface enables re-use of at least portions of the same apertured surface with at least six different cells.

* * * * *